(12) United States Patent
Seligman

(10) Patent No.: US 8,612,011 B2
(45) Date of Patent: Dec. 17, 2013

(54) RECIPIENT-CONTROLLED FITTING OF A HEARING PROSTHESIS

(75) Inventor: Peter Seligman, Essendon (AU)

(73) Assignee: Cochlear Limited, Macquarie University, NSW (AU)

( * ) Notice: Subject to any disclaimer, the term of this patent is extended or adjusted under 35 U.S.C. 154(b) by 673 days.

(21) Appl. No.: 12/358,122

(22) Filed: Jan. 22, 2009

(65) Prior Publication Data
US 2009/0240307 A1 Sep. 24, 2009

(30) Foreign Application Priority Data
Jan. 22, 2008 (AU) ................................ 2008900293

(51) Int. Cl.
*A61N 1/36* (2006.01)
*A61N 1/08* (2006.01)

(52) U.S. Cl.
USPC .................. 607/55; 607/56; 607/57; 607/137

(58) Field of Classification Search
USPC ............................................ 607/55–57, 137
See application file for complete search history.

(56) References Cited

U.S. PATENT DOCUMENTS

| | | | |
|---|---|---|---|
| 4,498,461 A | 2/1985 | Hakansson | |
| 4,532,930 A | 8/1985 | Crosby et al. | |
| 4,904,233 A | 2/1990 | Hankansson et al. | |
| 4,953,112 A | 8/1990 | Widin et al. | |
| 5,095,904 A * | 3/1992 | Seligman et al. | 607/57 |
| 5,271,397 A | 12/1993 | Seligman et al. | |
| 5,277,694 A | 1/1994 | Leysieffer et al. | |
| 5,824,022 A * | 10/1998 | Zilberman et al. | 607/57 |
| 6,157,861 A | 12/2000 | Faltys et al. | |
| 6,205,360 B1 | 3/2001 | Carter et al. | |
| 6,289,247 B1 * | 9/2001 | Faltys et al. | 607/57 |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,697,674 B2 | 2/2004 | Leysieffer | |
| 6,879,860 B2 | 4/2005 | Wakefield et al. | |

(Continued)

FOREIGN PATENT DOCUMENTS

| | | |
|---|---|---|
| WO | WO 2004/080532 | 9/2004 |
| WO | WO 2005/029915 | 3/2005 |

OTHER PUBLICATIONS

Takagi, H., "Interactive Evolutionary Computation: Fusion of the Capabilities of EC Optimization and Human Evaluation," Proceedings of the IEEE, Sep. 2001, vol. 89, No. 9, pp. 1275-1296, Aug. 1, 2001.

(Continued)

*Primary Examiner* — Joseph Stoklosa
(74) *Attorney, Agent, or Firm* — Kilpatrick, Townsend & Stockton, LLP.

(57) ABSTRACT

A method for fitting to a recipient a cochlear prosthesis having a sound processor that processes received sound in accordance with a MAP, the method comprises providing, by the hearing prosthesis, combinations of voice prompts and test stimuli for testing values of an element of the MAP; receiving from the recipient an indication of which of said values are desirable; and revising the MAP with the desired value for the tested element. A neural-stimulating device for stimulating nerve cells of a recipient is provided.

18 Claims, 4 Drawing Sheets

(56) References Cited

U.S. PATENT DOCUMENTS

| | | |
|---|---|---|
| 7,074,222 B2 | 7/2006 | Westerkull |
| 7,343,021 B2 | 3/2008 | Takagi et al. |
| 2003/0133578 A1 | 7/2003 | Durant |
| 2004/0181266 A1 | 9/2004 | Wakefield et al. |
| 2005/0107845 A1* | 5/2005 | Wakefield et al. ............. 607/57 |
| 2005/0137650 A1* | 6/2005 | Litvak et al. .................... 607/57 |
| 2010/0152813 A1 | 6/2010 | Lineaweaver et al. |
| 2010/0280307 A1* | 11/2010 | Lineaweaver et al. .......... 600/25 |

OTHER PUBLICATIONS

"International Search Report for PCT/US2004/07400", Aug. 27, 2004.
"Written Opinion for PCT/US2004/07400", Aug. 27, 2004.
Forrest, "Genetic Algorithms: Principles of Natural Selection Applied to Computation," Science, Aug. 13, 1993, vol. 261 (5123), pp. 872-878.
International Preliminary Report on Patentability for PCT/US2004/07400, dated Mar. 29, 2005.

* cited by examiner

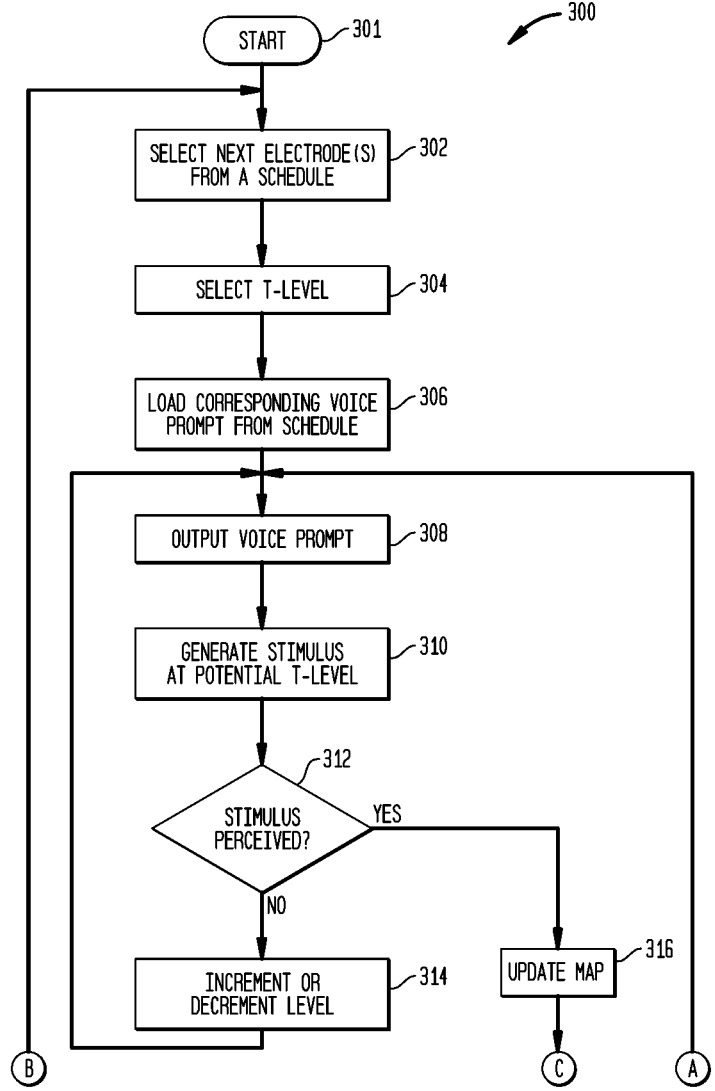

RECIPIENT-CONTROLLED FITTING OF A HEARING PROSTHESIS

CROSS-REFERENCE TO RELATED APPLICATIONS

This application claims priority to AU Provisional Application No. 2008900293 entitled "OPTIMISATION OF A HEARING DEVICE," filed Jan. 22, 2008 and commonly owned. This application is hereby incorporated by reference herein in their entirety.

BACKGROUND

1. Field of the Invention

The present invention relates generally to hearing prostheses, and in particular, to recipient-controlled fitting of a hearing prostheses.

2. Related Art

A hearing aid is an electroacoustic hearing prosthesis which is usually located in or behind the ear of the recipient (also referred to as a patient, wearer or user). Hearing aids are designed to receive acoustic sound, electronically amplify and modify the received sound, and output the amplified and modified sound acoustically into the recipient's ear canal to assist a hearing-impaired recipient perceive the sound.

Another type of hearing prosthesis is the cochlear implant, sometimes referred to herein as the cochlear prosthesis. Cochlear prostheses bypass the outer ear, the middle ear and the hair cells in the cochlea, by directly delivering electrical stimulation to the auditory nerve fibers. This enables the brain to perceive a hearing sensation resembling the natural hearing sensation normally delivered to the auditory nerve. U.S. Pat. No. 4,532,930 provides a description of one type of cochlear prosthesis.

For these and other hearing prostheses, software used in a sound processor is usually individually tailored to optimize the perceptions presented to a particular recipient. For example, many speech processing strategies rely on a customized "MAP" which provides, for a particular recipient, the threshold levels (T-levels) and comfortable levels (C-levels) of stimulation for each frequency band. Once the MAP is established, the sound processor may then optimally process received acoustic sound for that recipient.

Individual tailoring or programming a hearing prosthesis is traditionally performed by an audiologist using a fitting system. Determining T levels and C levels, for example, involves the audiologist following a programming routine involving application of a series of test stimuli and asking the recipient to provide responses based on whether each test stimuli is perceptible, or is too loud.

This fitting process may be repeated at times subsequent to the initial fitting to more accurately configure the hearing prosthesis to the recipient. Subsequent fitting of a hearing prosthesis may be performed to adapt prosthesis operation to a subsequent deterioration in the recipient's residual hearing capability, or the recipient's change in perception of sounds processed by the prosthesis. This may be due to, for example, the recipient not understanding speech well, sounds which are too loud or too soft, if the recipient needs to wear the sound processor at too high or too low a microphone sensitivity setting, if sounds are too harsh, or if certain sounds become annoying to the recipient. Recipients of a hearing prosthesis often use a single prosthesis for many years, so that such reconfiguration can be extremely important to ensure optimal performance of the prosthesis over time.

SUMMARY

In accordance with one embodiment of the present invention a method for fitting to a recipient a cochlear prosthesis having a sound processor that processes received sound in accordance with a MAP, the method comprises providing, by the hearing prosthesis, combinations of voice prompts and test stimuli for testing values of an element of the MAP; receiving from the recipient an indication of which of said values are desirable; and revising the MAP with the desired value for the tested element.

BRIEF DESCRIPTION OF THE DRAWINGS

Embodiments of the present invention are described herein with reference to the accompanying drawings, in which:

FIG. 3A is a flowchart illustrating the operations performed in a recipient-controlled fitting process, in accordance with one embodiment of the present invention.

DETAILED DESCRIPTION

Figure 1:
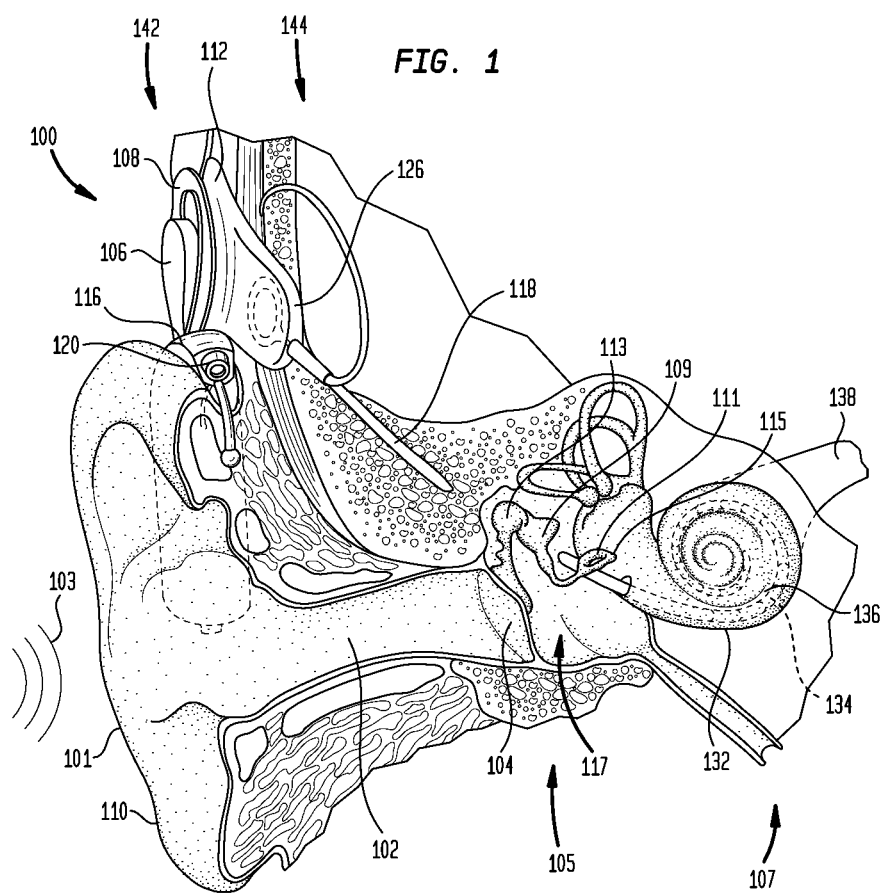
FIG. 1 is a perspective view of a cochlear prosthesis implanted in a recipient, in accordance with one embodiment of the present invention.

Embodiments of the present invention may be implemented in, and may include, hearing prostheses that generate acoustic stimulation, such as hearing aids; mechanical stimulation, such as middle ear implants; and electrical stimulation, such as cochlear implants. Embodiments of the present invention will be described below with reference to an exemplary hearing prosthesis, a cochlear implant. FIG. 1 is a perspective view of an exemplary cochlear implant in which embodiments of the present invention may be advantageously implemented.

The relevant components of outer ear 101, middle ear 105 and inner ear 107 are described next below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient. External assembly 142 typically comprises one or more audio pickup devices (e.g., microphone(s)) 120 for detecting sound, a speech processing unit 116, a power source (not shown), and an external transmitter unit 106. External transmitter unit 106 comprises an external coil 108 and, preferably, a magnet (not shown) secured directly or indirectly to the external coil 108. Speech processing unit 116 processes the output of audio pickup device (e.g., microphone) 120 that is positioned, in the depicted embodiment, by ear 110 of the recipient. Speech processing unit 116 generates coded signals, referred to herein as a stimulation data signals, which are provided to external transmitter unit 106 via a cable (not shown). Sound processing unit 116 is, in this illustration, constructed and arranged so that it can fit behind outer ear 101 (e.g., the auricle) and, as such, is referred to at times as a Behind-The-Ear (BTE) Sound Processing Unit or, more simply, a BTE unit. Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlea 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to ear 110 of the recipient.

Further details of the above and other exemplary prosthetic hearing implant systems in which embodiments of the present invention may be implemented include, but are not limited to, those systems described in U.S. Pat. Nos. 4,532,930, 6,537, 200, 6,565,503, 6,575,894 and 6,697,674. For example, while cochlear prosthesis 100 is described as having external components, in alternative embodiments, cochlear prosthesis 100 may be a totally implantable prosthesis. In one exemplary implementation, for example, speech processing unit 116, including the microphone, speech processor and/or power supply may be implemented as one or more implantable components. In one particular embodiment, speech processing unit 116 may be contained within the hermetically sealed housing used for speech processing unit 116.

In one example, electrode array 134 may include a plurality of independent electrodes each of which may be independently stimulated. For example, in an embodiment, employing Cochlear's Nucleus® 24 system, electrode array 134 includes 22 independent electrodes each of which stimulates a distinct area of the basilar membrane 136 of the recipient's cochlea 132. As one of ordinary skill in the art is aware, low-frequency sounds stimulate the basilar membrane most significantly at its apex, while higher frequencies more strongly stimulate the basilar membrane's base. Thus, electrodes of electrode array 134 located near the base of the cochlea are used to simulate high frequency sounds while electrodes near the apex are used to simulate low frequency sounds. Typically, in such a system, speech processing unit 116 stimulates only the electrodes with the largest signals. For example, system 100 may estimate the outputs for each of the 22 electrodes and select the ones with the largest amplitude (i.e., maxima). The number of maxima selected may vary, for example, between five (5) and ten (10), depending on a variety of factors. Moreover, the rate of stimulation, often referred to in units of pulses per second (pps), may also vary. Each of the applied maxima will be referred to herein as a channel of stimulation (or stimulation channel). Thus, in an example in which 8 maxima are applied, the system will be described as applying eight (8) channels of stimulation.

As one of ordinary skill in the art will appreciate, the present invention may be used in combination with any speech strategy now or later developed, including but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. The present invention may also be used with other speech coding strategies now or later developed. In one embodiment, the present invention may be used on Cochlear Limited's Nucleus™ implant system that uses a range of coding strategies alternatives, including SPEAK, ACE™, and CIS. Among other things, these strategies offer a trade-off between temporal and spectral resolution of the coded audio signal by changing the number of frequency channels chosen in the signal path. (NUCLEUS is a registered trademark of Cochlear Limited, Lane Cove, NSW, Australia. ACE is a trademark of Cochlear Limited, Lane Cove, NSW, Australia).

Once implanted, cochlear prosthesis 100, as well as other hearing prostheses, is typically adjusted to suit the specific needs of the recipient. As the dynamic range for electrical stimulation is relatively narrow and varies across recipients and electrodes, there is a need to individually tailor the characteristics of electrical stimulation for each recipient. This procedure, often referred to as "configuring," "fitting," "programming," "mapping" ("fitting" herein) involves measuring and controlling the amount of electrical current delivered to the cochlea. Typically, a clinician, audiologist or other medical practitioner (generally and collectively referred to as "audiologist" herein) uses interactive software and computer hardware to perform audiology measurements and create individualized programs, commands, data, settings, parameters, instructions, and/or other information (generally and collectively referred to as "ELEMENTS" and a "MAP" herein) that define the specific characteristics used to generate the electrical stimulation signals presented to the electrodes of the implanted electrode assembly.

The MAP is thereafter used by the sound processor to control the amount of electrical current delivered to each electrode, as well as to select which electrodes to stimulate corresponding to the respective sound signal. The MAP may also include the speech processing strategy and parameters of that strategy, when to switch between different strategies, and other functions and parameters. In some hearing prostheses, different MAPS may be applied in different situations/environments such as home, car, classroom, theatre etc. As such, each sound processor unit may store more than one MAP.

As noted, a hearing prosthesis is generally fit to a recipient at about the time when the prosthesis is initially implanted or provided to the recipient. This initial fitting is typically followed by subsequent fitting procedures. Such "refitting" procedures are required to more accurately tailor the prosthesis to the patient, or to accommodate one of a variety of dynamic circumstances such as the subsequent deterioration in the recipient's residual hearing capability, or the recipient's change in perception of sounds processed by the prosthesis.

Figure 2:
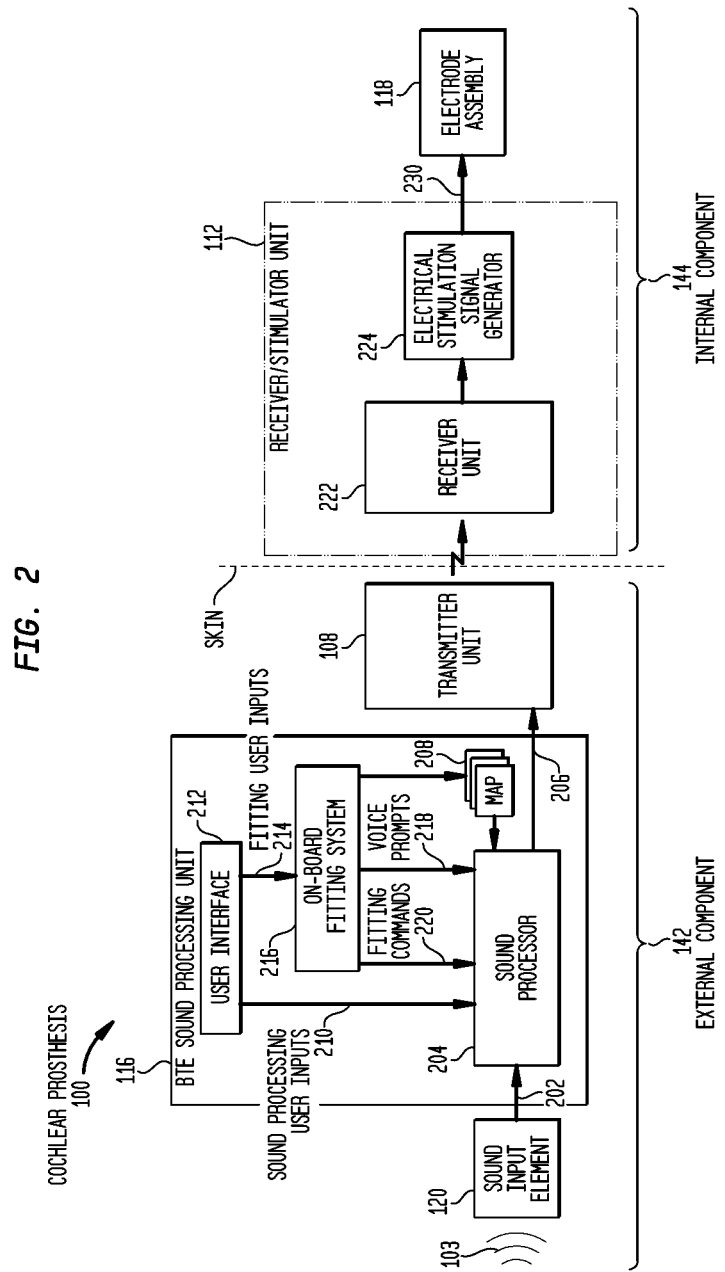
FIG. 2 is a functional block diagram of the cochlear prosthesis illustrated in FIG. 1, in accordance with one embodiment of the present invention.

In the illustrative embodiment, cochlear implant 100 provides the recipient with the ability to perform a fitting procedure to program their own sound processor; that is, to create a MAP, without requiring an audiologist or the hardware utilized by an audiologist. FIG. 2 is a functional block diagram illustrating an embodiment of hearing prosthesis, cochlear prosthesis 100, configured to enable the recipient to perform fitting procedures to refit the MAP stored in the recipient's sound processing unit. In this specific example, the recipient-controlled fitting process is performed using the embodiment of cochlear implant 100 illustrated in FIG. 2.

In the illustrative embodiment, cochlear prosthesis 100 comprises an external component 142, and an internal component 144, and noted above with reference to FIG. 1. External component 142 comprises one or more sound input elements 120 for detecting sound, a behind-the-ear (BTE) sound processing unit 116, a power source (not shown), and an external transmitter unit 108. Internal component 144 comprises receiver/stimulator unit 112 containing a receiver unit 222 and electrical stimulation signal generator 224. Receiver unit 222 is inductively coupled to transmitter unit 108 to receive energy and data via an RF link. The encoded stimulation data is provided to stimulation signal generator 224 which generates stimulation signals for the appropriate electrodes disposed on electrode assembly 118.

In operation, microphone 120 receives a sound signal 103 and generates an electrical output signal 202 representing the sound. Microphone 120 may be one of number of sound input elements now or later developed which may be utilized. Electrical signal 202 is provided to sound processing unit 116 which converts the signal into encoded data signals sa206 which are transmitted to internal component 144 as described herein. More specifically, in the illustrative embodiment of FIG. 2, electrical signal 202 is provided to a sound processor 204 which filters the electrical signal into its frequency components for signal processing in accordance with MAP 208 and sound processing user inputs 210 generated by user interface 212 in response to recipient actions.

The encoded data signals 206 are then provided to transmitter unit 108 where the signals are transmitted to stimulator/receiver unit 112 in internal component 144. Internal receiver unit 222 provides the transmitted electrical stimulation signals to stimulator unit 224. Stimulator unit 224 decodes the signals and generates electrical stimulation signals 230 which are provided to electrode assembly 118 for delivery to the recipient, thereby stimulating auditory nerve 138 (FIG. 1).

In this embodiment, an on-board fitting system 216 is implemented as one or more software programs that are executable on sound processor 204 of BTE sound processing unit 116. It should be appreciated that on-board fitting system 216 may be implemented in other cochlear prostheses and, more generally, other hearing prostheses, such as cochlear implants having a body worn controller. Such components of hearing prostheses include a user interface containing mechanical, graphical/software, wireless and/or voice activated user controls, generally and collectively referred to herein as user interface 212.

Fitting system 216 comprises a voice synthesizer to generate a spoken word stimulus to the recipient which is perceived by the recipient as a spoken word instruction, such as "Press button if you can hear this sound." In one embodiment, this is performed by fitting system 216 generated voice prompts 218 to sound processor 204. Such voice prompts may be stored in an accessible memory and retrieved by fitting system 216 as needed. The content of the voice prompts depends on the parameter, setting or function that is being refitted, while the format of the voice prompts depends on in which part of processing pipeline the prompts will be provided. It should be appreciated, however, that fitting system 216 may cause cochlear prosthesis 100 to generate perceptible voice commands by storing the stimulation signals for such commands and providing them to transmitter unit 108.

In the illustrative embodiment, fitting system 216 uses the recipient's own existing MAP so that the spoken word stimulus is as comprehensible as possible, and in some embodiments stores files containing the stimulation patterns. This method is efficient in terms of data storage and does not require the filtering portions of sound processor 204 to be running during programming. Alternative embodiments may instead store audio files for playback via the filtering portions of the sound processor. For example, fitting system 216 may merely require that prosthesis 100 have the capability to store appropriate spoken word stimulus files, and to invoke the appropriate refitting process. Consequently, embodiments of the present invention enable a recipient to undertake recipient-controlled refitting on such a sound processor and/or remote control. The remote control or processor could have a very small display if required for other purposes or need not even have a display at all, because the recipient would not need to see the display for those embodiments of the refitting process in which all instructions from fitting system 216 are delivered by the voice prompts.

Figure 3B:
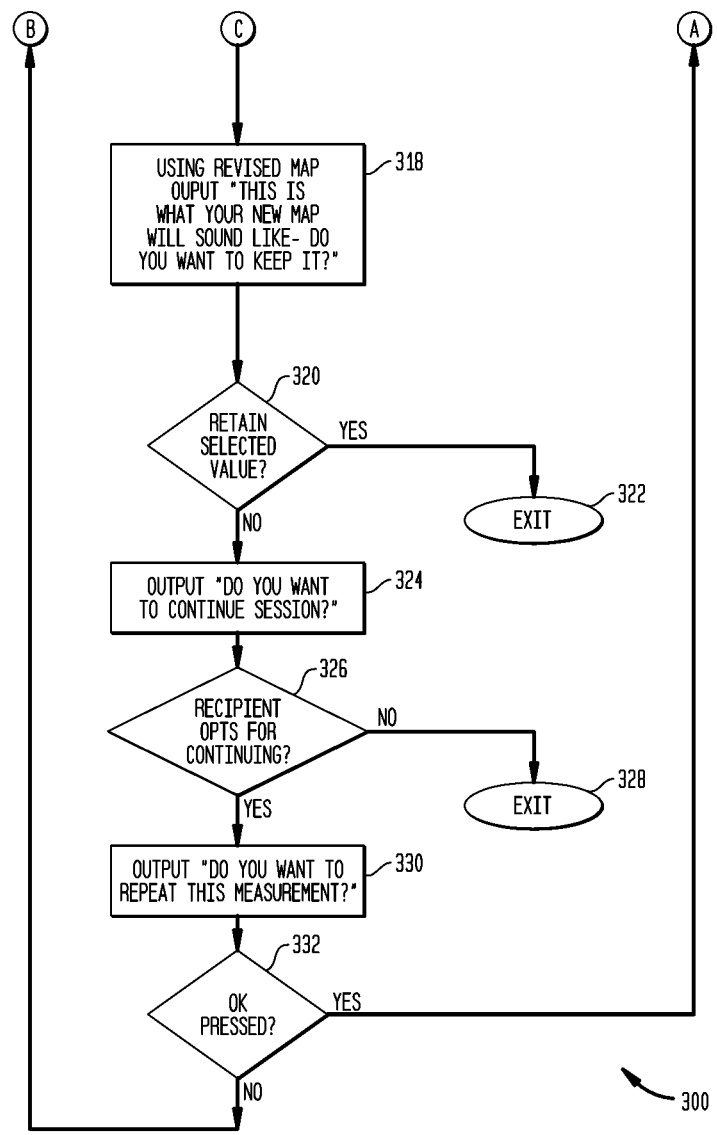
FIG. 3B is a flowchart illustrating the operations performed in a recipient-controlled fitting process, in accordance with one embodiment of the present invention.

FIGS. 3A-3B are a flow chart of one embodiment of a recipient-controlled fitting process 300 of the present invention. It should be appreciated that embodiments of the present invention may be implemented to refit any or all settings, functions and parameters as may be customizable for each recipient or hearing prosthesis which is/are stored in a MAP 208. For ease of description, fitting process 300 will be described with reference to a specific parameter, the threshold or T-Level parameter. It should be appreciated by those of ordinary skill in the art that similar or analogous processes may be implemented to adjust other settings, functions and parameters stored in a MAP 206, and all such processes and operations are within the scope of the present invention.

Recipient-controlled fitting process 300 is initiated at start block 301. In one embodiment, such initiation may be in response to a recipient action, such as the recipient entering a command, such as a button press, on user interface 212 of BTE sound processing unit 116. For example, process 300 may be initiated on request by pressing a particular hardware or software "MAP" button on cochlear implant 100. Alternatively, fitting process 300 may be initiated as a matter of course at start-up when sound processing unit 116 is initially powered, initially turned off, or at some other power-state change, or at some predetermined or specified time, such as in the evening when the recipient retires for the night, and/or at some known idle time when, for example, the recipient is usually commuting by public transport.

Following initiation of fitting process 300, at block 302 an electrode or group of electrodes 136 is selected from a schedule which may be programmed or stored in connection with on-board fitting system 216. For the selected electrode(s) 134, at block 304 a parameter is selected by the recipient or automatically by fitting system 216 in accordance with a predetermined schedule. In this example, the T-level parameter is selected, whether by the recipient or by fitting system 216.

At block 306 a corresponding voice prompt is loaded from memory based on a stored schedule. At block 308, the voice prompt is output for perception by the recipient. For T-level mapping, for example, the voice prompt may comprise the electrode stimulations necessary for the recipient to perceive the spoken word stimulus: "Press OK if you hear a tone", followed at block 310 with the application of a stimulus at an initial potential T-level by the selected electrode(s).

Fitting process 300 then determines at block 312 whether the recipient perceived the stimulus, for example, by receiving an indication from user interface 212 that a designated button was pressed. If process 300 determines that the recipient did not perceive the applied stimulus then at block 314 process 300 is directed to increment the T-level and to return to block 308. If at block 312 it is determined that the recipient perceived the applied stimulation, then processing continues at block 316 at which MAP 208 is updated. Otherwise the potential T-Level in incremented at block 314 and the process returns to block 308.

Routine 300 continues on FIG. 3B via flow chart connector C.

At block 318 process 300 outputs a voice prompt which is perceived by the recipient as the spoken word stimulus "This is what your new MAP will sound like; press OK if you want to keep it". The recipient is then given an opportunity to listen to operation of the sound processor using MAP 208 at the selected T-level. It should be appreciated that there are numerous other approaches that may be implemented to give the recipient an opportunity to confirm whether the selected value for the parameter is indeed the value that the recipient would prefer to maintain.

Fitting process 300 checks at block 320 whether the recipient confirmed the selected parameter value. This may be communicated by any user interface means including the pressing of a designated hardware or software button. If confirmed, process 300 exits at block 322. It should be appreciated that since this example is limited to the refitting of the T-Level parameter, such a confirmation may cause process 300 to exit. However, process 300 may be expanded to include the same or additional operations to refit other values stored in MAP 208, or the exiting of a routine that executes process 300 may return to or cause the execution of another process that will provide the recipient with the opportunity to proceed to another parameter, setting or function selection.

If the selected parameter value is not to be maintained, then process 300 continues at block 324 at which process 300 causes the generation of a spoken word stimulus to the recipient "Do you want to continue the session?" If at block 326 the recipient fails to the desire to continue, or indicates to not continue, then processing processed to block 328 at which process 300 exits.

If at block 326 it is determined that the recipient indicated that the refitting process 300 is to continue, then at block 330 process 300 causes the generation of a spoken word stimulus to the recipient "Do you want to repeat this measurement?"

If at block 332 it is determined that the recipient responded in the affirmative, then processing continues at block 308 via flowchart connector A to repeat the same stimulus to the same electrode(s). On the other hand, if at block 332 it is determined that the recipient does not want to repeat the measurement, then processing continues at block 302 via flowchart connector B to select a new electrode or group of electrodes for refitting.

For fitting the T-Level, the level would be increased gradually until a threshold was reached, much as is done on a conventional programming system, but without requiring clinical hardware or a clinician. The voice instructions would then ask the recipient to press the button when the test sound was comfortably loud (for C-Levels), or just audible (for T-levels). After each electrode(s) has been checked, the program would automatically step to the next electrode(s), in this embodiment, after asking the recipient (at block 326) if the recipient wanted to move to the next stage of mapping.

By enabling the recipient to carry out refitting at a time and location the recipient chooses, embodiments of the present embodiment reduce the likelihood of a recipient suffering from poor device performance due to difficulties or clinical attendance for refitting. Regular refitting is likely to provide improved performance of each such cochlear prosthesis and increased acceptance by prospective recipients. Moreover, by enabling recipients to undertake self refitting, clinics' burden of refitting sessions may be ameliorated, freeing up such resources, for example, to see increased numbers of new prospective patients.

It is anticipated that initial programming of an implanted cochlear prosthesis will be performed by an audiologist, with subsequent refitting being independently performed by the recipient. Alternatively, it may be desirable for some refitting to occur under professional guidance to ensure the recipient is provided with optimal mapping. For example it may be desirable to have the recipient perform a certain number of refitting sessions and then return to the clinic when a further refitting is required to ensure ongoing clinical involvement in optimizing prosthesis performance. Under this approach, recipients do not need to regularly visit a center with expensive fitting hardware and software.

Moreover, in the embodiment described herein, the refitting of cochlear prosthesis 100 need not be completed in one session. As such, portions of MAP 208 may be refitted at successive sessions until the entire MAP is refitted. Or, perhaps, if a particular aspect of the cochlear prosthesis is not performing optimally, then only the corresponding MAP 208 or portion of a MAP 208 may be refitted. For example, MAP 208 could be progressively updated on a daily basis such that for a 22 electrode cochlear prosthesis any given T-level or C-level would be checked once every 44 days. Such progressive refitting is impractical in arrangements requiring clinical visits.

While requiring storage of appropriate spoken word stimulus files, such voice prompts are nevertheless advantageous in exploiting the existing sound processing capability of such a hearing prosthesis, obviating the need for any special hardware or clinical expertise in order to implement the refitting process 300. Due to the suitability of refitting for automation, embodiments of the present invention may permit use of a very small number of simple voice prompts, such as a set of prompts comprising: press the program button if this sound (beep) is too loud, press the program button if this sound (beep) is comfortable; press the program button if this sound (beep) is soft; press the button if no sound follows this prompt; press the button if you hear a sound following this prompt. It is to be noted that in conducting the test of the present embodiment for a recipient who is severely or profoundly deaf, there is no need to be in a quiet environment. This is because the hearing prosthesis could simply block sound received via the microphone so that the deaf recipient would not hear anything except the required prompts and test signals.

It will be appreciated by persons skilled in the art that numerous variations and/or modifications may be made to the invention as shown in the specific embodiments without departing from the spirit or scope of the invention as broadly described. For example, other methods of stimulation could consist of stimulating a group of electrodes using an internally generated signal, and allowing the recipient to control the loudness using a volume control of the same type they use in their everyday life. In another mode, a group of electrodes could be stimulated at a level which would represent a desired target threshold for quiet sounds. The recipient could control the loudness using a volume control of the same type they use in their everyday life. Appropriate voice prompts in accordance with the present invention would not burden the recipient with the need for advanced clinical knowledge but would instead make it clear what the recipient was required to do.

In other embodiments, such self-controlled refitting using voice prompts could be supplemented by visual prompts shown on a prosthesis remote control screen for example or on a mobile phone screen.

Moreover, such self-controlled refitting need not be restricted to measurement of threshold and comfortable levels, but could include the choice of program and adjustment within one program. For example the recipient may be prompted by spoken word stimulus to press a button if a program sounds too sharp or too muffled or the like.

In some embodiments the recipient may be empowered to exit process 300 at any time by providing a recipient input for the recipient to switch back to operation of their main program once the recipient is happy with the settings or want to terminate a programming session. It is desirable that the recipient be equipped with some experience with the speech/sound processing at least to the point that the recipient can follow the prompts. To assist in this the prompts could be provided in writing at the outset, so that the recipient does not have to be able to identify the prompts in an open-set sense.

The voice prompts can be stored in a number of formats. Examples are in a wav file, MP3 or other compressed form, or as a sequence of stimulation pulses, specifying an electrode and amplitude, to then be mapped using the appropriate T and C levels.

Moreover, while the present embodiment has been described in relation to a cochlear prosthesis, embodiments of the present invention could be used to enable reprogramming of hearing aids, DACS (Direct Acoustic Stimulation) devices, or a hybrid of a cochlear prosthesis and hearing aid.

In some embodiments, a maximum limit may be imposed on the regularity with which refitting is conducted, in order to prevent the recipient from altering the fitting too often.

The stimuli perceptible to the recipient as being spoken word instructions, referred to herein as spoken word stimuli, may comprise instructions, explanations and the like in the recipient's spoken language of choice. The spoken word stimuli are preferably derived from stored data of the hearing device, whether onboard or stored in an associated device such as a body worn controller or remote control. For example the hearing prosthesis may comprise a storage device such as a random access memory storing audio files which can be played back acoustically by a hearing aid, or which can be converted into appropriate electrical stimuli applicable by to a cochlear implant, for perception by the recipient. Additionally or alternatively, where the hearing device prosthesis is comprises a cochlear implant, the storage device may hold files containing the electrode stimulus patterns required to elicit a spoken word perception by a cochlear implant recipient.

The test stimuli preferably comprise stimuli appropriate to determine, in accordance with the programming routine, the T and C levels of the user recipient in each of a plurality of frequency bands. The programming routine may be any appropriate routine for example as applied clinically by audiologists.

The user input in response to the spoken word stimuli may comprise simply pressing a button. For example the spoken word stimuli may convey a message such as "Press the button if you hear a sound after this prompt". In such embodiments the user interface may be as simple as a simple button which permits implementation of the invention using existing hearing device hardware for example a behind-the-ear controller or body-worn controller having at least one user input button.

By providing for spoken word prompts, the present invention may obviate the need for a graphic display for a user to view during reprogramming. Consequently, reprogramming may in some embodiments be effected using only the existing hardware of the hearing device without need for connection to a separate device having a graphic display for the user to view. Moreover, by providing for the hearing device itself to implement the programming routine, the present invention permits a user to achieve device reprogramming without need for internet connection or a visit to a clinic.

Additionally or alternatively, for users with adequate enunciation the user input in response to the spoken word stimuli may comprise verbal speech for detection by a microphone of the hearing device and for recognition by appropriate software of the speech processor. For example the spoken word stimuli may convey a message such as "Say yes if you hear a sound after this prompt". Appropriate speech recognition capability would be required in the processor in such embodiments.

Additionally or alternatively, the user input in response to the spoken word stimuli may comprise adjusting a volume control dial, for example to enable the user to respond to a spoken word stimuli such as "Adjust the volume until the following tone is the loudest which is comfortable, then click ok" or "Adjust the volume until the following tone is the quietest you can hear, then say ok".

Where the hearing device comprises a cochlear implant of a profoundly deaf user, the device preferably ceases to process acoustic sounds from the surrounding environment during execution of the programming routine. Such embodiments ensure that the user perceives complete silence except for the spoken voice stimuli and programming routine stimuli generated as part of the programming routine, allowing accurate perception by that user of T levels and C levels or the like. Such embodiments enable profoundly deaf users to achieve appropriate reprogramming even in acoustically noisy environments.

The programming routine may be initiated by the user at times selected by the user. Alternatively, initiation of the programming routine may be controlled by the device to occur at predetermined times, such as at power off and/or at power on.

In some embodiments of the invention, the programming routine may comprise partial reprogramming of the device, for example by reprogramming only one T level or C level. Such embodiments enable progressive reprogramming of the device over time, and may represent a lesser time imposition on the user by enabling the user to gradually effect reprogramming over the course of several short reprogramming sessions rather than requiring the user to dedicate a single lengthy period to achieve a complete reprogramming in one sitting.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for fitting a recipient-worn hearing prosthesis to a recipient, the hearing prosthesis having an audio pickup device configured to detect sound, an on-board fitting system, and a sound processor configured to process the detected sound in accordance with a MAP, the method comprising:
   stimulating the recipient's auditory nerve with a test stimulation signal;
   detecting directly, with the hearing prosthesis, speech from the recipient indicating a result of said stimulation; and
   adjusting the MAP, via the on-board fitting system, in response to the directly detected speech.

2. The method of claim 1, wherein said adjusting the MAP comprises:
   adjusting one or more of programs, commands, data, settings, parameters and instructions used to generate electrical stimulation signals applied by said hearing prosthesis.

3. The method of claim 1, further comprising:
   receiving input via an interface unit of said hearing prosthesis; and
   adjusting the MAP, via the on-board fitting system, in response to said input.

4. The method of claim 3, wherein said receiving input via the interface unit comprises:
   receiving input via one or more mechanical controls positioned on an external component of said hearing prosthesis.

5. The method of claim 3, wherein said receiving input via the interface unit comprises:
   receiving input via a graphical user interface (GUI).

6. The method of claim 1, further comprising:
   stimulating the recipient's auditory nerve with signals configured to be perceived by the recipient as a voice prompt.

7. The method of claim 6, further comprising:
   retrieving at least one of a plurality of audio files stored in a data storage device; and
   stimulating the recipient's auditory nerve with signals configured to be perceived by the recipient as a voice prompt using the at least one of said audio files.

8. The method of claim 1, wherein adjusting the MAP, via the on-board fitting system, comprises:
   executing one or more software programs on the sound processor to adjust the MAP.

9. A method for fitting a cochlear implant to a recipient, the cochlear implant comprising a behind-the-ear (BTE) sound processing unit having an audio pickup device configured to detect sound, an on-board fitting system, and a sound processor configured to process detected sound in accordance with a MAP, the method comprising:
   providing, via the cochlear implant, a voice prompt and a test stimulation signal to the recipient;
   detecting directly, with the BTE sound processing unit, speech from the recipient indicating a result of said stimulation; and
   adjusting the MAP, via the on-board fitting system, in response to the directly detected speech.

10. The method of claim 9, wherein said adjusting the MAP comprises:
    adjusting one or more of programs, commands, data, settings, parameters and instructions used to generate electrical stimulation signals applied by said hearing prosthesis.

11. The method of claim 9, wherein adjusting the MAP, via the on-board fitting system, comprises:
    executing one or more software programs on the sound processor to adjust the MAP.

12. The method of claim 9, further comprising:
    stimulating the recipient's auditory nerve with signals configured to be perceived by the recipient as a voice prompt.

13. The method of claim 9, further comprising:
    retrieving at least one of a plurality of audio files stored in a data storage device; and
    stimulating the recipient's auditory nerve with signals configured to be perceived by the recipient as a voice prompt using the at least one of said audio files.

14. A method for fitting a cochlear implant to a recipient, the cochlear implant comprising a behind-the-ear (BTE) sound processing unit having an audio pickup device configured to detect sound, an interface unit, an on-board fitting system, and a sound processor configured to process detected sound in accordance with a MAP, the method comprising:
    providing, via the cochlear implant, a voice prompt and a test stimulation signal to the recipient;
    detecting directly, with the audio pickup device of the BTE, speech from the recipient indicating a result of said stimulation; and
    adjusting the MAP, via the on-board fitting system, in response to the directly detected speech.

15. The method of claim 14, wherein said adjusting the MAP comprises:
    adjusting one or more of programs, commands, data, settings, parameters and instructions used to generate electrical stimulation signals applied by said hearing prosthesis.

16. The method of claim 14, further comprising:
    receiving input via one or more mechanical controls of the interface unit positioned on the BTE; and
    adjusting the MAP, via the on-board fitting system, in response to the input.

17. The method of claim 14, further comprising:
    receiving input via a graphical user interface (GUI) of the interface unit; and
    adjusting the MAP, via the on-board fitting system, in response to the input.

18. The method of claim 14, further comprising:
    disregarding sound detected by the audio pickup device while providing the test stimulation signal to the recipient.

* * * * *